United States Patent
Feng et al.

(10) Patent No.: US 10,096,108 B2
(45) Date of Patent: Oct. 9, 2018

(54) MEDICAL IMAGE SEGMENTATION METHOD AND APPARATUS

(71) Applicants: Yuan Feng, Northborough, MA (US); Long Huang, Northborough, MA (US)

(72) Inventors: Yuan Feng, Northborough, MA (US); Long Huang, Northborough, MA (US)

( * ) Notice: Subject to any disclaimer, the term of this patent is extended or adjusted under 35 U.S.C. 154(b) by 195 days.

(21) Appl. No.: 15/387,886

(22) Filed: Dec. 22, 2016

(65) Prior Publication Data
US 2018/0114313 A1    Apr. 26, 2018

(51) Int. Cl.
| G06K 9/62 | (2006.01) |
| G06T 7/11 | (2017.01) |
| G06T 7/00 | (2017.01) |
| A61B 5/00 | (2006.01) |
| A61B 6/00 | (2006.01) |
| G06K 9/46 | (2006.01) |
| G06K 9/52 | (2006.01) |

(52) U.S. Cl.
CPC .......... *G06T 7/0012* (2013.01); *A61B 5/7264* (2013.01); *A61B 6/5217* (2013.01); *G06K 9/4642* (2013.01); *G06K 9/52* (2013.01); *G06K 9/6215* (2013.01); *G06K 9/6218* (2013.01); *G06K 9/6223* (2013.01); *G06T 7/11* (2017.01); *G06K 2009/4666* (2013.01)

(58) Field of Classification Search
CPC .. A61B 5/7264; A61B 6/5217; G06K 9/4642; G06K 9/52; G06K 9/6215; G06K 9/6218; G06K 2009/4666; G06T 7/0012; G06T 7/11

See application file for complete search history.

(56) References Cited

U.S. PATENT DOCUMENTS

| 2009/0067726 A1* | 3/2009 | Erol | G06F 17/30247 382/197 |
| 2012/0076422 A1* | 3/2012 | Yang | G06K 9/6211 382/201 |
| 2014/0126804 A1* | 5/2014 | Ding | G01N 21/8806 382/141 |
| 2014/0254919 A1* | 9/2014 | Sun | G06K 9/3233 382/154 |
| 2015/0073765 A1* | 3/2015 | Boettger | A61B 5/7275 703/11 |
| 2017/0076114 A1* | 3/2017 | Rai | G06F 21/6254 |

OTHER PUBLICATIONS

Dubuisson et al. ("A modified Hausdorff distance for object matching," Proceedings of 12th International Conference on Pattern Recognition, Oct. 9-13, 1994) (Year: 1994).*

* cited by examiner

*Primary Examiner* — Yubin Hung
(74) *Attorney, Agent, or Firm* — SZDC Law P.C.; Feng Shan

(57) ABSTRACT

A medical image segmentation method includes: step 1, initialize of the number of clusters and determine the initial values of the cluster centroids; step 2, calculate a Hausdorff distance between each cluster centroid and each pixel in the image; step 3, calculate a membership function of each pixel based on the Hausdorff distance and a Euclid distance between the cluster centroids and each pixel; step 4, calculate an objective function, cluster the pixels of the image based on the updated membership function, and update the centroid value; and repeating step 2-4, until a difference between two objective function values is less than a threshold value. Then the membership function from the last iteration is a final segmentation.

9 Claims, 3 Drawing Sheets

MEDICAL IMAGE SEGMENTATION METHOD AND APPARATUS

This application claims priority to Chinese Patent Application No. 201610913874.5, filed Oct. 20, 2016, which is incorporated by reference for all purposes as if fully set forth herein.

FIELD OF THE INVENTION

The field of this invention is image processing. More particularly, the invention relates to a medical image segmentation method and apparatus.

BACKGROUND

As the development of medical imaging technology, image processing methods have been widely used in medical research and clinical applications, such as radiotherapy planning, intervention treatment, and surgical guidance. Image segmentation is one of the important topic in medical image processing. It can help the clinician to segment and extract the region of interest (pathological tissues etc.) for further analyzing and quantification, which can increase the accuracy and efficiency of clinical diagnosis. However, because of the variety and complexity of the medical images, image segmentation poses a great challenge.

Among the image segmentation method used clinically, thresholding method is the most widely used because of its simple implementation and small computational load. Its algorithm is to set different threshold based on different image features and grouping the image pixels into several categories. Mostly used features include grayscale values of the image, color image features, or the features transformed from the original gray scale images or color images. However, when there are many different soft tissues in one image with low contrast, the thresholding method could not segment the images. Also, it is very sensitive to noise. Therefore, it is usually used to segment blood cells or CT images but not all types of images or soft tissues.

Other image segmentation method include template-based method, which needs additional contour template information. This could not be used to segment soft tissues which has a relatively large difference or deformation compared to template and those which are not included in the template.

SUMMARY OF THE INVENTION

The present invention is to overcome the above shortages of the image segmentation method, to provide a method to segment several different soft tissues when the image contrast is low, which is suitable to segment general soft tissues in medical images.

To solve the above technical problems, the present invention provides a medical image segmentation method that includes the following steps:

Step 1, initialize of the number of clusters and determine the initial values of the cluster centroids;

Step 2, calculate the Hausdorff distance between the cluster centroids and each pixel in the image;

Step 3, calculate the membership function of each pixel based on the Hausdorff and Euclid distances between the cluster centroids and each pixel;

Step 4, calculate the objective function, cluster the pixels of the image based on the updated membership function, and update the centroid value;

Repeat step 2-4, until the difference between the two objective function values is less than the threshold value. Then the membership function from the last iteration is the final segmentation.

The present invention adopted a fuzzy clustering method to segment medical images, which can utilize the gray scale pixel information and the contrast information from the original images, while considering the computation efficiency and the performance. The invention can be used to segment images with low contrast and blurred boundaries, and is suitable for all kinds of soft tissues. Besides, using the pixel difference defined by the Hausdorff distance, the invention can effectively use the neighbor information. This can categorize the boundary information with blurry pixels that is especially useful for images with blurred boundaries and low image contrast Another aspect of the invention is to use the image histogram to initialize the cluster centroid value that has the same distance.

Another aspect of the invention is to calculate the Hausdorff distance between each image pixel and the centroids, which includes the following steps:

Select several neighbor regions with the image pixel at the center, calculate the mutual information between the neighbor region and the centroid;

Select the neighbor region that has the maximum mutual information value to calculate the Hausdorff distance;

Calculate the Hausdorff distances between each centroid and the neighbor region with the pixel at the center.

The present invention can compare neighboring region of each image pixel with different contrast and select a proper neighbor region for calculation. The adaptive algorithm can resolve the discontinuity of the boundaries and those with large contrast jumps.

Another aspect of the invention includes the several neighbor regions that comprises of the rectangular region with a width and height of 3, 5, and 7 pixels.

Another aspect of the invention is to calculate the mutual information between the neighbor region and the centroids with $$I = \sum_{i \in A} \sum_{j \in B} p(i,j) \log \frac{p(i,j)}{p(i)p(j)},$$

where p(i,j) is the joint distribution function of the two images, and p(i), p(j) are the pixel distribution function for each image, respectively.

Another aspect of the invention is to calculate the Hausdorff distance between the centroids and the selected neighbor region with the equation of $$d_H(A, B) = \max\left\{ \sup_{p_i \in A} \inf_{p_j \in B} |p_j - p_i|, \sup_{p_j \in B} \inf_{p_i \in A} |p_i - p_j| \right\},$$

where A is the cluster centroid, B is the pixels within the selected region.

Another aspect of the invention is to calculate the membership function of each pixel baesd on the Hausdorff and Euclid distance with the equation of $$u_{ik} = \frac{(\|x_i - v_k\|^2 + \alpha\|x_i - v_k\|_H^2)^{-\frac{1}{m-1}}}{\sum_{l=1}^{C}(\|x_i - v_l\|^2 + \alpha\|x_i - v_l\|_H^2)^{-\frac{1}{m-1}}},$$

where $x_i$ is the gray scale pixel value, $v_k$ is the centroid, c is the amount of centroids, $\alpha$ is the empirical parameter determined by the image resolution and contrast, m is 2, $\|x_i-v_k\|$ is the Euclid distance between each pixel and the centroids, $\|x_i-v_k\|_H$ is the Hausdorff distance between each pixel and the centroids.

The present invention calculates the membership function of each pixel based on the Hausdorff distance and Euclid distance. The clustering process is more accurate and the features of each specific image can determine the value of $\alpha$. Therefore, the algorithm is robust to noise and is capable to segment blurred boundaries.

Another aspect of the invention includes the objective function of $J=\sum_{i=1}^{n}\sum_{k=1}^{c}u_{ik}^{m}\|x_i-v_k\|^2+\alpha\sum_{i=1}^{n}\sum_{k=1}^{c}u_{ik}^{m}\|x_i-v_k\|_H^2$, where n is the number of the image pixels, c is the amount of centroids, $x_i$ is the gray scale pixel value, $v_k$ is the centroid, $\alpha$ is the empirical parameter, m is 2, $\|x_i-v_k\|$ is the Euclid distance between each pixel and the centroids, $\|x_i-v_k\|_H$ is the Hausdorff distance between each pixel and the centroids.

The present invention calculates the objective function based on both the Hausdorff and Euclid distance. The value of $\alpha$ can be determined by different images, therefore enhancing the robustness of the algorithm to noise and the capability to resolve blurry boundaries.

Another aspect of the invention includes the centroid updating equation $$v_k = \frac{\sum_{i=1}^{n} u_{ik}^m x_i}{\sum_{i=1}^{n} u_{ik}^m},$$

where $x_i$ is the gray scale pixel value, $v_k$ is the centroid, n is the number of the image pixels, and m is 2.

Accordingly, the present invention also provided an image segmentation apparatus, which has features including:

A first processing module, for executing step 1, determines the initial cluster number and calculates the initial value of each centroid;

A second processing module, for executing step 2, calculates the Hausdorff distance between each pixel and the centroids;

A third processing module, for executing step 3, calculate the membership function based on the Hausdorff distance and Euclid distance between each pixel and the centroids;

A fourth processing module, for executing step 4, calculate the objective function, re-iterate the clustering process based on the updated membership function;

A fifth processing module, for iteration of the above steps of 2-4, until the differences of the objective function is less than the threshold value, and the last membership functions obtained provide the segmentation results.

Wherein, the second processing module includes:

A first processing unit, with each pixel located at the center of its neighbor region, calculates the mutual information between several different neighbor region and the centroids;

A second processing unit, which is used to select the neighbor region with the maximum value of the mutual information to calculate the Hausdorff distance;

A third processing unit, which is used to calculate Hausdorff distance between each centroid and the neighbor region with the pixel located at the center.

In conclusion, the present invention has the following advantages:

1. By adopting a fuzzy clustering method to segment medical images, the method can utilize the gray scale image information and the contrast value while taking into account of the balance of computation efficiency and performance. Therefore, the method can be used to segment all kinds of soft tissues and organs with low contrast and blurry boundaries. Besides, by defining the pixel difference using Hausdorff distance, the method can use the neighbor information of each pixel, especially those with low contrast, to segment the blurry boundaries.

2. The present invention can compare neighboring region of each image pixel with different contrast and select a proper neighbor region for calculation. The adaptive algorithm can resolve the discontinuity of the boundaries and those with large contrast jumps.

3. The pixel membership function and the objective function are calculated based on both the Hausdorff and Euclid distances. Therefore, the clustering of each pixel is more accurate. At the same time, the value of $\alpha$ can be determined and adjusted by different images, enhancing the robustness of the algorithm and the capability of resolving blurry boundaries.

DETAILED DESCRIPTION OF THE ILLUSTRATED EMBODIMENTS

The invention will be further illustrated in more detail with reference to accompanying drawings. It is noted that, the following embodiments are intended for purposes of illustration only and are not intended to limit the scope of the invention. Any other embodiments based on the present inventions without other innovative work are also within the protection of the present invention.

In medical image research and application, only parts of the image or certain regions are of interest to scientists or clinicians. These usually include certain organs or tissues. In order to distinguish the objects for analysis, we need to extract the regions of interest out of the image for further analysis and processing. Image segmentation is a process to extract the regions of interest with different features out of an image. The features could be the gray scale level, color, or the textures of an image. The regions of interest could be a single region or different regions.

However, in clinical applications, automatic image segmentation has several challenges. For example, the influences of noise, blurry features, shades and shadows can result in erroneous segmentation. Therefore, automatic image segmentation is an improving technique. In the present medical image, the boundaries between different tissues are usually not shape with blurred features. With the commonly used thresholding method, the segmentation of regions is very rigid and distinctive, which cannot accurately describe the boundaries that may or may not belong to a certain region. Therefore, it cannot deal with the uncertainly features in the medical images.

In order to better describe or distinguish the pixels in medical images that has uncertainty features, the present invention adopted a segmentation method based on fuzzy clustering theory. By calculate the membership function of each pixel, the algorithm can determine the pixel belongings adaptively, therefore resulting in a better and robust segmentation.

Figure 1:
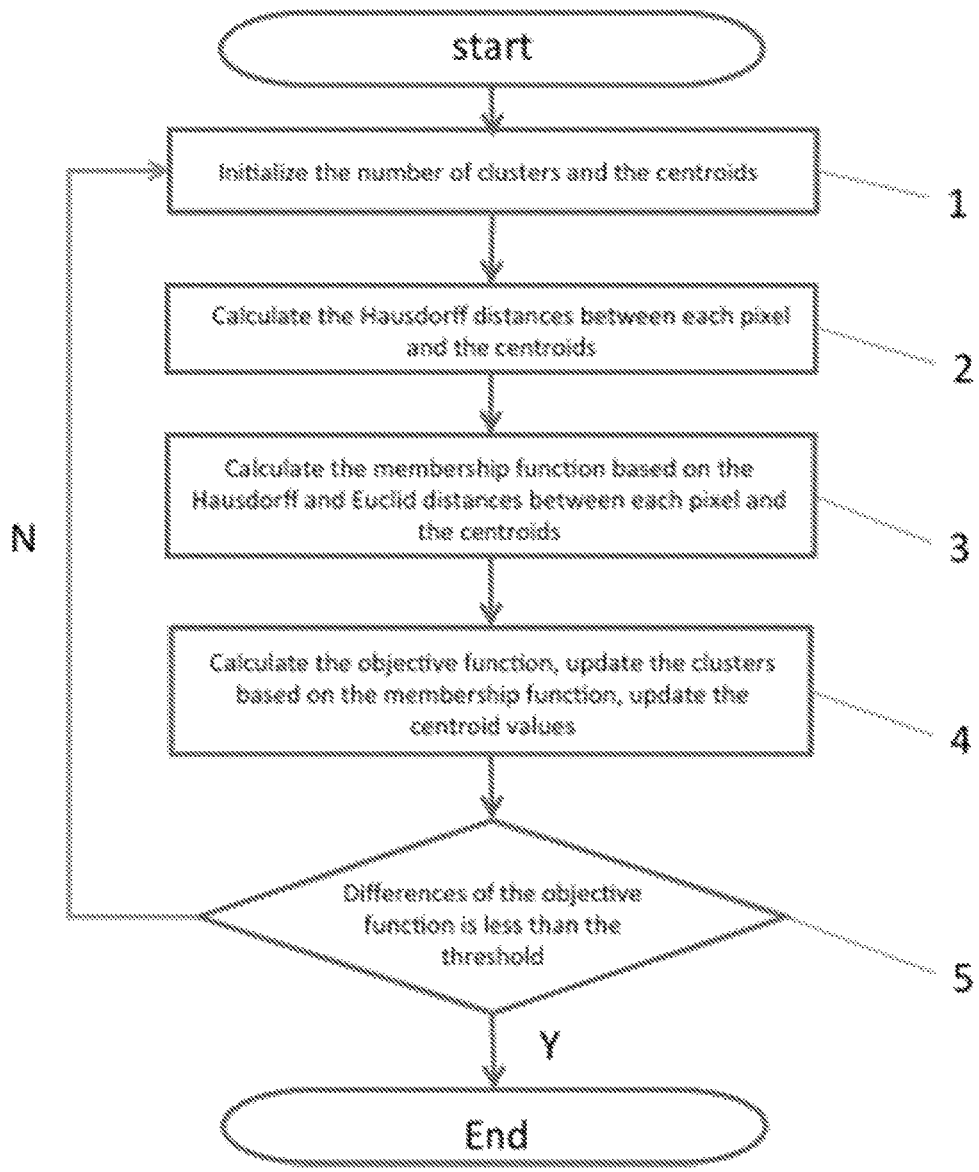
FIG. 1 is a flow chart of the medical image segmentation algorithm of the present invention.

FIG. 1 is the flow chart of a medical image segmentation method of the present invention, which includes the following steps:

Step 1, initialization of the cluster number and determine the initial values of the cluster centroids;

The image segmentation method of the present invention is to first determine the cluster number. This is to determine how many parts or regions of interests are to be segmented and the pixels included. The initialization of the cluster number and the centroids are determined by the specific image features and the desired segmentation results, such as the histogram of the image. Once determined, the number of the clusters is not to be changed in the following segmentation process. However, the pixels included in each cluster are constantly changing and updating, which is the process of clustering.

Once the cluster number and the pixels inside each cluster are determined, the cluster centroids can be calculated. The cluster centroids are values that can be interpreted as an abstract mean value of a certain region of pixels. It is not a physical pixel point in an image. There are many ways to calculate the initial values of the centroids, preferably, the present invention use the image histogram to calculate the initial value that has the same distance between each value.

Step 2, calculate the Hausdorff distance between the cluster centroids and each pixel in the image;

The present invention uses Hausdorff distance, which is a definition of distance between two sets, to calculate the distance between each centroid and pixels. The Hausdorff distance defined pixel difference can utilize the neighbor information of each pixel. This is effective to segment and cluster the soft tissue boundaries, especially those with low image contrast.

Figure 2:
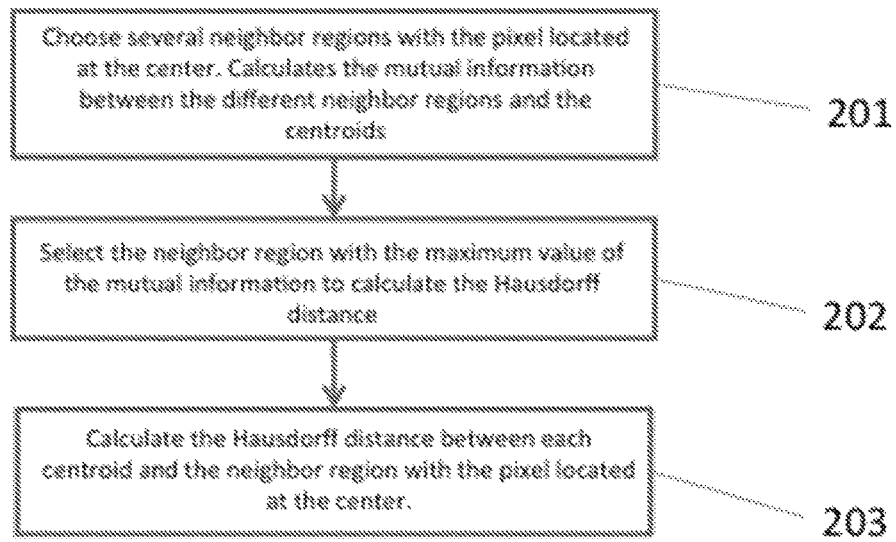
FIG. 2 is a flow chart to calculate the Hausdorff distance between each image pixel and the cluster centroids.

FIG. 2 is a flow chart to calculate the Hausdroff distance between each image pixel and the centroids, which includes the following steps:

Step 201, select several neighbor regions with the image pixel at the center, calculate the mutual information between the neighbor region and the centroid;

In medical image analysis, the neighbor region of one pixel is defined by a set of pixel points surrounding the pixel that is located at the center. The region is usually a circle or rectangle whose size determined by selection. Therefore, the computation of the pixel is determined by its neighbor region, which is called neighbor calculation.

In a preferred example, the present invention has selected the neighbor region that comprises of the rectangular region with a width and height of 3, 5, and 7 pixels. That is, rectangular region having 9, 25, and 49 pixels.

Once the neighbor region is determined, the present invention use equation $$I = \sum_{i \in A} \sum_{j \in B} p(i, j) \log \frac{p(i, j)}{p(i)p(j)}$$

to calculate the mutual information between the neighbor region and the centroids, where p(i,j) is the joint distribution function of the two images, p(i) is the pixel distribution function for the neighbor region, and p(j) is the pixel distribution function for the pixel.

Step 202, select the neighbor region that has the maximum mutual information value to calculate the Hausdorff distance;

Among all the mutual information values, select the neighbor region that has the maximum value to calculate the Hausdorff distance. For example, in the previously stated rectangular region with a width and height of 3, 5, and 7 pixels, if the region with a width and height of 5 pixels has the largest mutual information, then the Hausdorff distance is calculated based on the 5 pixel neighbor region. By comparing different regions, the neighbor region is selected adaptively, therefore solving the problem of discontinuity and contrast jump in the boundaries.

By utilizing the mutual information to determine the neighbor region size, not only the neighbor information is used but also the Hausdorff distance was satisfied. Therefore, the blurry boundaries and regions were estimated by this similarity defined, improving the segmentation effects.

Step 203, Calculate the Hausdorff distances between each centroid and the neighbor region with the pixel at the center.

Once the neighbor region is determined by the maximum mutual information, the present invention calculates the Hausdorff distances between each centroid and the neighbor region with the pixel at the center. The equation to calculate Hausdorff distance is $$d_H(A, B) = \max\left\{\sup_{p_i \in A} \inf_{p_j \in B} |p_j - p_i|, \sup_{p_j \in B} \inf_{p_i \in A} |p_i - p_j|\right\},$$

where A is the cluster centroid, B is the pixels within the selected region. The present invention use the Hausdorff distance to determine the pixel differences, which can utilize the neighbor information and the soft tissues with low contrast values, therefore effectively segment and cluster the blurry boundaries.

Step 3, calculate the membership function of each pixel based on the Hausdorff and Euclid distances between the cluster centroids and each pixel;

In fuzzy clustering, in order to describe the extent of belongings of each pixel, or the probability of the belongings of each pixel, the idea of membership function is introduces. Each membership function provides a value between 0 and 1 for each pixel, describing the pixel belongings. The sum of all the membership function values of each one of the pixel is 1. For example, if there exist three clusters A, B, and C, and the membership function of x is {0.7, 0.2, 0.1}, this represents that the probabilities of the pixel belongs to cluster A, B, and C are 70%, 20%, and 10%, respectively.

In the present invention, the membership function is $$u_{ik} = \frac{(\|x_i - v_k\|^2 + \alpha \|x_i - v_k\|_H^2)^{-\frac{1}{m-1}}}{\sum_{l=1}^{C} (\|x_i - v_l\|^2 + \alpha \|x_i - v_l\|_H^2)^{-\frac{1}{m-1}}},$$

where $x_i$ is the gray scale pixel value, $v_k$ is the centroid, c is the amount of centroids, α is the parameter to adjusting the weighting of the Hausdorff distance that can be determined by the image contrast and resolution. For example, in MR images with high contrast and resolution, the scope of the parameters could be 30-50; for blurry and low contrast ultrasound image, the value could be 40-60; moreover, the parameter can balance the membership function and objective function representing the neighbor region information. m is the fuzziness value that is taken as 2 in this invention, $\|x_i-v_k\|$ is the Euclid distance between each pixel and the centroids, $\|x_i-v_k\|\|_H$ is the Hausdorff distance between each pixel and the centroids.

In the present invention, the membership function is calculated by both the Euclid and Hausdorff distance, by ultiziing the difference between each pixel and its neighbor region, the rigid clustering between each pixel and the soft clustering are combined, generating a more effective segmentation of the features, which is especially suitable for segmentation images with low contrast and blurry boundaries.

Step 4, calculate the objective function, cluster the pixels of the image based on the updated membership function, and update the centroid value;

In fuzzy clustering method, an objective function is needed. In each iteration, the objective function is calculated and compared with the last iteration. If the difference is small enough, then a robust segmentation results is achieved after the clustering. In the present invention, the objective function is $J=\Sigma_{i=1}^{n}\Sigma_{k=1}^{c}u_{ik}^{m}\|x_i-v_k\|^2+\alpha\Sigma_{i=1}^{n}\Sigma_{k=1}^{c}u_{ik}^{m}\|x_i-v_k\|_H^2$, where n is the number of the image pixels, c is the amount of centroids, $x_i$ is the gray scale pixel value, $v_k$ is the centroid, α is the empirical parameter, m is the fuzziness parameter, $\|x_i-v_k\|$ is the Euclid distance between each pixel and the centroids, $\|x_i-v_k\|_H$ is the Hausdorff distance between each pixel and the centroids.

At the same time, after the calculation of the membership function as mentioned above, the final cluster determination of each pixel can decided by the membership function. Usually, the maximum membership function value determines the corresponding final cluster. For example, if there is three clusters A, B, C. the pixel x has membership function value of {0.7, 0.2, 0.1}. 0.7 is the maximum membership function, therefore x belongs to cluster A. If the updated membership function values are {0.3, 0.6, 0.1}, then 0.6 becomes the largest value, then x belongs to B. In this manner, all the pixels can be clustered and group based on the membership functions.

Based on the re-grouped pixels, the centroids are updated accordingly by the equation $$v_k = \frac{\sum_{i=1}^{n} u_{ik}^m x_i}{\sum_{i=1}^{n} u_{ik}^m},$$

where $x_i$ is the gray scale pixel value, $v_k$ is the centroid, n is the number of the image pixels, and m is the fuzziness value. In this invention, the m value is taken as 2.

Step 5, repeat step 2-4 for at least twice until the difference between the two objective function values is less than the threshold value. Then the clustering has come to a constant result and the membership function from the last iteration is the final segmentation. If the difference between the two objective functions is larger than the threshold value, then repeat the above steps 2-4 until converge. Preferably, the threshold value is set to $10^{-6}$.

Figure 3:
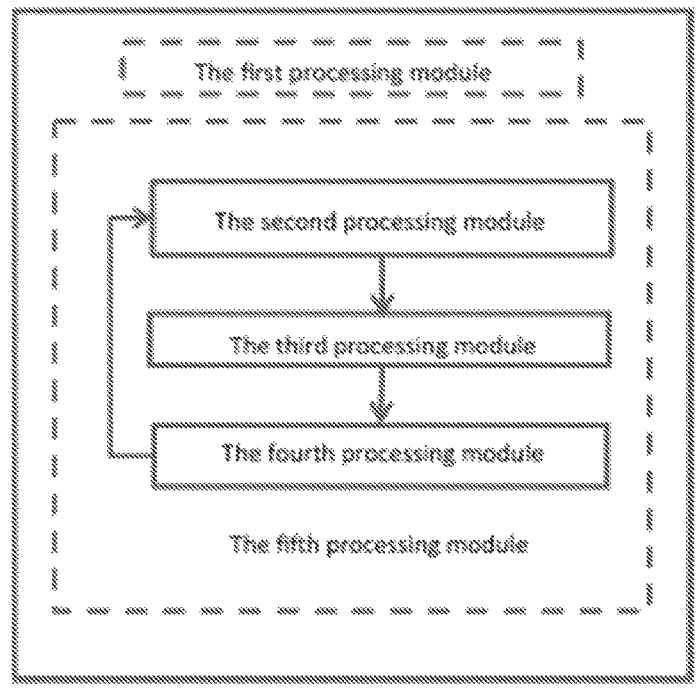
FIG. 3 is a schematic view of the medical image segmentation apparatus of the present invention.

FIG. 3 is a schematic view of a medical image segmentation apparatus of the present invention, which comprised of:

A first processing module, for executing step 1, determines the initial cluster number and calculates the initial value of each centroid; this module is used for initializing the parameters, including cluster number and the initial values of the centroids.

A second processing module, for executing step 2, calculates the Hausdorff distance between each pixel and the centroids; the Hausdorff distance is the distance between two point sets.

A third processing module, for executing step 3, calculate the membership function based on the Hausdorff distance and Euclid distance between each pixel and the centroids, calculate the probability of each pixel belonging to each of the cluster.

A fourth processing module, for executing step 4, calculate the objective function and determines whether to end the iteration or not; re-cluster the pixels based on the membership function and update the values of the centroids for the next iteration;

A fifth processing module, for iteration of the above steps of 2-4, until the differences of the objective function is less than the threshold value, and the last membership functions obtained provide the segmentation results.

Figure 4:
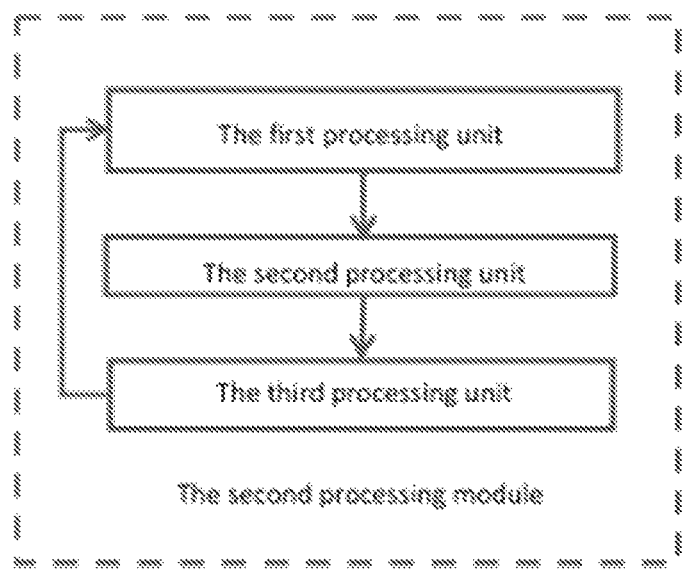
FIG. 4 is a schematic view of the second processing module of the present invention.

FIG. 4 shows the second processing module of the present invention, which includes:

A first processing module, with each pixel located at the center of its neighbor region, calculates the mutual information between several different neighbor region and the centroids; wherein the neighbor regions are rectangular regions with a width and height of 3, 5, and 7 pixels. That is, rectangular region having 9, 25, and 49 pixels.

A second processing module, which is used to select the neighbor region with the maximum value of the mutual information to calculate the Hausdorff distance; automatically select the best neighbor region to calculate the Hausdorff distance, therefore solve the problem of discontinuities boundary and large variations of image contrast.

A third processing module, which is used to calculate Hausdorff distance between each centroid and the neighbor region with the pixel located at the center. By using the Hausdorff distance defined pixel difference, the neighbor region is effectively utilized. This is especially suitable to segment the soft tissues with low image contrast and can cluster and segment the blurry boundaries.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A medical image segmentation method, which comprises the following processing steps:
   step 1, initialize the number of clusters and determine the initial values of cluster centroids;
   step 2, calculate a Pseudo-Hausdorff distance between each cluster centroid and each pixel in an image;
   step 3, calculate a membership function of each pixel being a member of a cluster based on the Pseudo-Hausdorff distance and an Euclid distance between each cluster centroid and said each pixel;

step 4, calculate an objective function, cluster the pixels of the image based on the membership function, and update the values of the cluster centroids; and repeat step 2-4, until a difference between the objective function values of two consecutive iterations is less than a threshold value, and then the membership function from the last iteration is a final segmentation.

2. The medical image segmentation method as claimed in claim 1, wherein the initial values of the cluster centroids are calculated by an image histogram where differences between each centroid are the same.

3. The medical image segmentation method as claimed in claim 1, wherein the step of calculating the Pseudo-Hausdorff distance between each cluster centroid and each image pixel comprises:

choose several neighbor regions with said each image pixel at the center, calculate a mutual information between each chosen neighbor region and the centroids;

select the neighbor region that has the maximum mutual information value; and calculate the Hausdorff distance between said each centroid and the selected neighbor region as the Pseudo-Hausdorff distance between said each cluster centroid and said each image pixel.

4. The medical image segmentation method as claimed in claim 3, wherein the several neighbor regions are defined by rectangular regions with a width and height of 3, 5, and 7 pixels.

5. The medical image segmentation method as claimed in claim 3, wherein mutual information between sets A and B are determined by $$I = \sum_{i \in A} \sum_{j \in B} p(i,j) \log \frac{p(i,j)}{p(i)p(j)},$$

where p(i,j) is the joint distribution function of sets A and B, p(i) and p(j) are the distribution functions for sets A and B, respectively.

6. The medical image segmentation method as claimed in claim 5, wherein the Hausdorff distance between sets A and B is calculated by $$d_H(A, B) = \max\left\{ \sup_{p_i \in A} \inf_{p_j \in B} |p_j - p_i|, \sup_{p_j \in B} \inf_{p_i \in A} |p_i - p_j| \right\},$$

and wherein the Pseudo-Hausdorff distance between a centroid $v_k$ and a pixel i with value $x_i$, $\|x_i - v_k\|_H$, is $d_H(A,B)$, with A being a set consisting of the centroid $v_k$ and B being a set consisting of values of the pixels belonging to the selected neighbor region centered at pixel i.

7. The medical image segmentation method as claimed in claim 6, wherein the membership function of each pixel is determined by the Pseudo-Hausdorff distance and Euclid distance between the pixel and the centroids, the equation for calculating the membership function is $$u_{ik} = \frac{(\|x_i - v_k\|^2 + \alpha \|x_i - v_k\|_H^2)^{-\frac{1}{m-1}}}{\sum_{l=1}^{C} (\|x_i - v_l\|^2 + \alpha \|x_i - v_l\|_H^2)^{-\frac{1}{m-1}}},$$

where $x_i$ is the gray scale value of pixel i, $v_k$ is the centroid, c is the amount of centroids, $\alpha$ is determined by the image resolution and contrast, $\|x_i - v_k\|$ is the Euclid distance between $x_i$ and $v_j$.

8. The medical image segmentation method as claimed in claim 7, wherein the objective function is $J = \sum_{i=1}^{n} \sum_{k=1}^{c} u_{ik}^m \|x_i - v_k\|^2 + \alpha \sum_{i=1}^{n} \sum_{k=1}^{c} u_{ik}^m \|x_i - v_k\|_H^2$ where n is the number of the image pixels, c is the amount of centroids, $x_i$ is the gray scale value of pixel i, $v_k$ is the centroid, $\alpha$ is the empirical parameter and m is 2.

9. The medical image segmentation method as claimed in claim 7, wherein the equation to calculate the updated centroids is $$v_k = \frac{\sum_{i=1}^{n} u_{ik}^m x_i}{\sum_{i=1}^{n} u_{ik}^m},$$

where $x_i$ is the gray scale value of pixel i $v_k'$ is the updated centroid of $v_k$, n is the number of the image pixels, and m is 2.

* * * * *